United States Patent [19]

Darboux et al.

[11] Patent Number: 4,991,970
[45] Date of Patent: Feb. 12, 1991

[54] METHOD FOR OPTIMIZING CONTRAST IN AN IMAGE OF A SAMPLE

[75] Inventors: Michel Darboux; Gilles Grand, both of Grenoble; Frédéric Moisan, Brest, all of France

[73] Assignee: Commissariat A L'Energie Atomique, Paris, France

[21] Appl. No.: 297,295

[22] Filed: Jan. 13, 1989

[30] Foreign Application Priority Data

Jan. 18, 1988 [FR] France .................................. 8800496

[51] Int. Cl.$^5$ ................................................. G01J 3/51
[52] U.S. Cl. ..................................... 356/402; 356/419; 382/65
[58] Field of Search ............... 356/402, 416, 418, 419; 382/65–68

[56] References Cited

U.S. PATENT DOCUMENTS 4,028,728  6/1977  Sharp .................................. 358/106

FOREIGN PATENT DOCUMENTS 60-181906  8/1986  Japan .................................. 356/402
WO87/01806  3/1987  World Int. Prop. O. .

OTHER PUBLICATIONS

The Journal IEEE Circuits and Devices Magazine—"Machine Vision Automates Inspection of Thick-Film Hybrids" by Valarie C. Bolhouse (Jan. 1986), pp. 44–48.
The Journal Feinwerktechnik Messtechnik—"Optische Halbleitermaterialprufung mit der Nikrosop-Spektralphotometrie" by Von Dr. P. Baurschmidt und Dipl.-Ing H. Scharf, Oberkochen (Dec. 1984), pp. 401–403.

Primary Examiner—Vincent P. McGraw
Attorney, Agent, or Firm—Pearne, Gordon, McCoy & Granger

[57] ABSTRACT

This invention concerns a method for optimizing contrast in an image of a sample.

This sample (5) comprises a whole number of zones having different reflection or transmittance factors. These zones are illuminated by a light source (7) and the image is obtained at the output of an optical system (4) to be analyzed by a sensor (10) supplying on the outputs recording signals of this image. Contrast optimization consists of determining the characteristics of an optimal fiber to be inserted between the source (7) and the sample (5) to be controlled.

Application in particular for the control of in-production integrated circuits.

6 Claims, 2 Drawing Sheets

METHOD FOR OPTIMIZING CONTRAST IN AN IMAGE OF A SAMPLE

FIELD OF THE INVENTION

The present invention concerns a method for optimizing contrast in an image of a sample having at least two adjacent zones with respectively two different reflection or transmittance factors.

BACKGROUND OF THE INVENTION

This invention more particularly applies to the optical control of structures made up of distinct uniform zones whose optical properties vary according to the length of the lighting wave. More particularly, the invention applies to the optical control of integrated circuits between certain production stages relating to these circuits. Inside an integrated circuit, each uniform zone in fact consists of, for example, silicon layers deposited on the substrate.

To obtain the image of a sample, it is known that it is generally necessary to use a light source which lights the sample and an optical system forming the image of this sample. For controlling microelectronic integrated circuits, the optical system used is a microscope. Recording of the image is effected at the output of the optical system (a microscope concerning the application in question) by means of an image sensor, such as a photographic plate for example, or a camera which supplies on its outputs recording signals corresponding to the image. Moreover, this camera may be a charge transfer type camera (known as a CCD camera—Charges Coupled device).

The contrast obtained in the image between the various uniform zones of the sample depends on the selected lighting type and in particular on the spectrum of wavelengths of this lighting in relation to the sample optical properties (reflection or transmittance).

It is extremely important, especially as regards the production control of integrated circuits, to obtain the best available contrast between two zones, for example, of an image of this circuit so as to be able to detect any possible production defects appearing more particularly at the limit of these zones.

Generally, control is effected by comparing a recorded image of the circuit to be controlled and the corresponding recorded image of a circuit regarded as perfect.

The simplest and most currently used means in microelectronics in order to obtain images displaying the various zones of a circuit is effected by means of reflected bright field microscopy. Lighting of the object is effected through the lens of a microscope under quasi-normal incidence on the circuit to be controlled.

The storing of images is effected in real time, for example by means of a video camera, namely a CCD type, coupled to acquisition electronics transferring the image into a data processing memory.

The defects are detected from the numerical difference between the numerical signals corresponding to the image acquired from the circuit to be controlled and from numerical signals corresponding to a corresponding reference image of a circuit regarded as faultless.

In these conditions, knowing that most of the production defects are constituted by inclusions from one zone into a nearby zone, it is obvious that obtaining in this case a good contrast between the various zones facilitates the detection of faults.

To optimize this contrast, a wavelength filtering is carried out of the light source which lights the sample. Contrast optimization is understood to mean determining the desired contrast, the latter not necessarily being maximum.

Currently, there is no automatic method making it possible to select a wavelength filtering of the source light, optimized according to the sample to be examined.

SUMMARY OF THE INVENTION

The object of the invention is to overcome these drawbacks and especially to provide a method wherein it is possible to automatically and rapidly obtain the characteristics of a filter enabling the desired contrast of the sample image to be obtained.

The invention concerns a method for optimizing the contrast of an image of a sample to be controlled having a whole number n of zones i, with $n \geq 2$, having different reflection or transmittance coefficients, these zones being lit by a light source and the image being obtained at the output of an optical system so as to be analyzed by a sensor supplying on outputs recording signals of this image, wherein it consists firstly of obtaining the image of the sample:

in order to define a set of functions $F(\lambda)$ each representing transmittance according to the wavelength of an optical filter to be inserted between the source and the sample, in order to calculate for these functions $F(\lambda)$ amplitude values $N_i(F\lambda)$, with $1 \leq i \leq n$, which would be equal to those of the corresponding output signals of the sensor respectively for each zone i of the sample with a transmittance filter $F(\lambda)$, these amplitudes being calculated from the relation:

$$N_i(F(\lambda)) = I(F(\lambda)) \int_A^B C(\lambda) \cdot M(\lambda) \cdot F(\lambda) \cdot R_i(\lambda) i_o(\lambda) d\lambda$$

in which:
$C(\lambda)$ denotes the sensor spectral responsivity,
$M(\lambda)$ denotes the spectral responsivity of the optical system,
$R_i(\lambda)$ denotes the spectral reflection or transmittance of the zone i,
$i(\lambda)$ denotes the source power spectral density,
$\lambda°$ A and $\lambda$ B are two previously selected limiting wavelengths,
$I(F(\lambda))$ is an attenuation factor calculated for each of the functions $F(\lambda)$ so that the illumination power of the sample is compatible with the effective functioning zone of the sensor $(I(F(\lambda)))$ and is between 0 and 1.
calculating for each function $F(\lambda)$ from the corresponding amplitudes $N_i$ the values of the factor Q defined by the equation:

$$Q_{ij} = \frac{N_i - N_j}{N_{sat}},$$

with $1 \leq I \leq n$ and $1 \leq j \leq n$ and $i < j$, each value of factor $Q_{ij}$ being representative of the contrast between the zones i and j and $N_{sat}$ denoting the highest amplitude signal value which the sensor can supply when it is saturated.

selectioning for each function $F(\lambda)$ a value of the factor $Q_{ij}$ corresponding to the desired contrast called the quality factor, selecting from amongst these quality factors the Q quality factor allowing for contrast to be optimized, this optimization supplying the transmission factor $F \lambda$) of the filter to be selected, inserting the selected filter between the source and the sample to be controlled so as to obtain the sample image.

According to another characteristic of the invention, the parameters $C(\lambda)$, $M(\lambda)$, $i_o(\lambda)$ are parameters supplied respectively with the sensor, the optical system and the source, $Ri(\lambda)$ being a parameter calculated from the optical parameters of each zone i of the sample, or calculated respectively during preliminary sampling of said sensors, optical system and source, or measured by means of a spectrophotometer prior to controlling the sample.

The optical parameters of a zone in the case of microelectronics are formed by the thickness and by the complex refractive index of the various layers constituting said zone. In the case where reflection or transmittance are measured by means of a high-speed spectrophotometer, the use of a high-speed spectrophotometer, for example, of the multichannel type, enables measurements to be made in real time.

According to another characteristic of the invention, for each function $F(\lambda)$, the attenuation factor $I(F(\lambda))$ is calculated so that the maximum value of the amplitudes $Ni(F(\lambda))$ is equal to the constant value $KN_{sat}$, with $0 < k \leq 1$, k being a predetermined value and $N_{sat}$ being the value of the highest amplitude value of the signal which may be supplied by the saturation sensor.

However, irrespective of the value of the attenuation factor $I(F(\lambda))$, which is between 0 and 1, the maximum value is always less than the selected value $KN_{sat}$, the value of I then being fixed at 1 (I=1).

According to another characteristic, the power factor $I(F\lambda))$ is calculated so that the average value of the amplitudes $NiF(\lambda)$ is equal to a fixed value $kN_{sat}$ with $0 < k \leq 1$.

According to another characteristic, the value of the quality factor Q allowing for optimization of the contrast is obtained by selecting for each function $F \lambda$) from amongst the value of the $Q_{ij}$ factors the minimum value of $Q_{ij}$ and by choosing the function $F(\lambda)$ corresponding to the maximum of these minimum values of $Q_{ij}$.

According to another characteristic, the value of the quality factor Q allowing for optimization of contrast is obtained by selecting for each function $F \lambda$) from amongst the values $Q_{ij}$ the maximum value of $Q_{ij}$ and by selecting the function $F(\lambda)$ corresponding to the minimum of these maximum values of $Q_{ij}$.

BRIEF DESCRIPTION OF THE DRAWINGS

The characteristics and advantages of the invention shall be more readily understood on reading the following description with reference to the annexed figures in which.

DETAILED DESCRIPTION OF THE PREFERRED EMBODIMENTS

Figure 1:
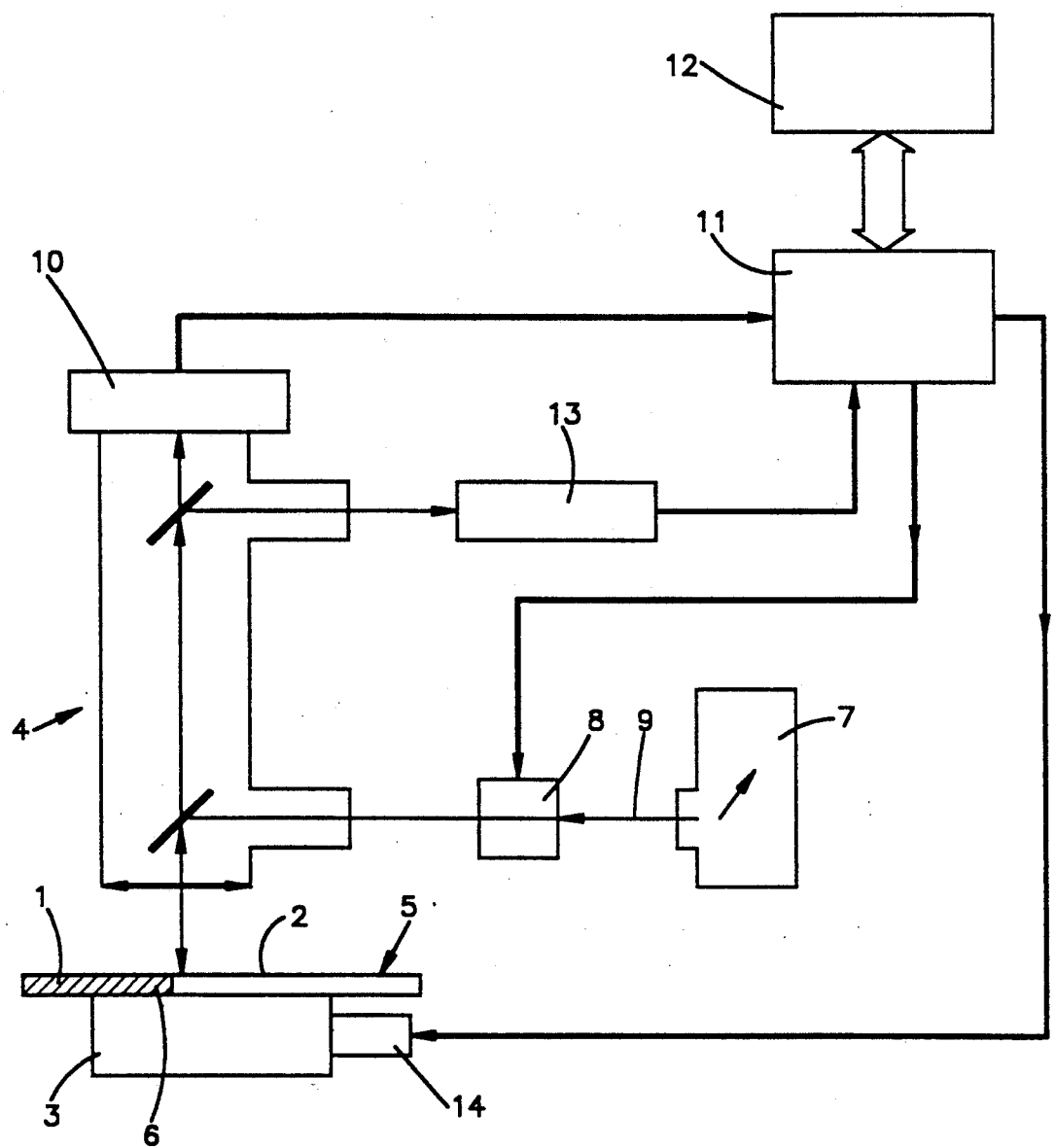
FIG. 1 diagrammatically shows a device enabling the method of the invention to be implemented.

The device diagrammatically illustrated on FIG. 1 comprises an optical system, such a microscope 4, on a mobile table 3 on which is placed a sample 5 to be controlled for which it is desired to obtain a reflectance image, for example. In the example shown on the figure, this sample has two zones 1, 2 whose microscopic dimensions are delimited by a boundary line 6, these two zones have different reflectance coefficients.

The sample 5 is illuminated, for example, by a white light source 7, whose intensity may be adjusted. When used for controlling the sample 5, the device comprises also a filtering device 8 inserted between the microscope 4 and the source 7 on the light beam 9 emitted by this source. The source thus illuminates the sample through the filtering device and one part of the microscope. This filtering device, as well as calculation of its functions $F(\lambda)$, shall be subsequently described in full.

The rays reflected by the sample 5 traverse the microscope 4 which supplies an image of the sample. A sensor 10, such as the video camera of the CCD type, transforms this image into video signals.

The signals supplied by the camera are applied to a computer 11, such as a microprocessor, so as to be recorded in the memory 12 of this microprocessor. This memory comprises also, as shall be fully described later, a program which makes it possible for the microprocessor to optimize contrast of the sample image 5 by selecting the function $F(\lambda)$ of the filtering device to be inserted between the source and the microscope during control of the sample.

This device also comprises a spectrophotometer 13 which receives through the microscope 4 rays reflected by the sample 5. The output signals of this spectrophotometer are applied to the microprocessor 11 so as to instantaneously calculate the coefficients of reflectance of the sample zones, as shall be seen later in full detail. In the example described, the reflection factor of the sample is supposed to have been determined. The same applies to determining transmittance: reflectance is determined from the luminous beam light reflected by the sample. Transmittance is determined from the light transmitted by the sample when the luminous beam of the source traverses the sample.

The method of the invention by means of this device consists of optimizing the contrast of the image of the sample to be controlled, this sample having at least two reflectance and transmittance zones 1, 2.

Figure 2:
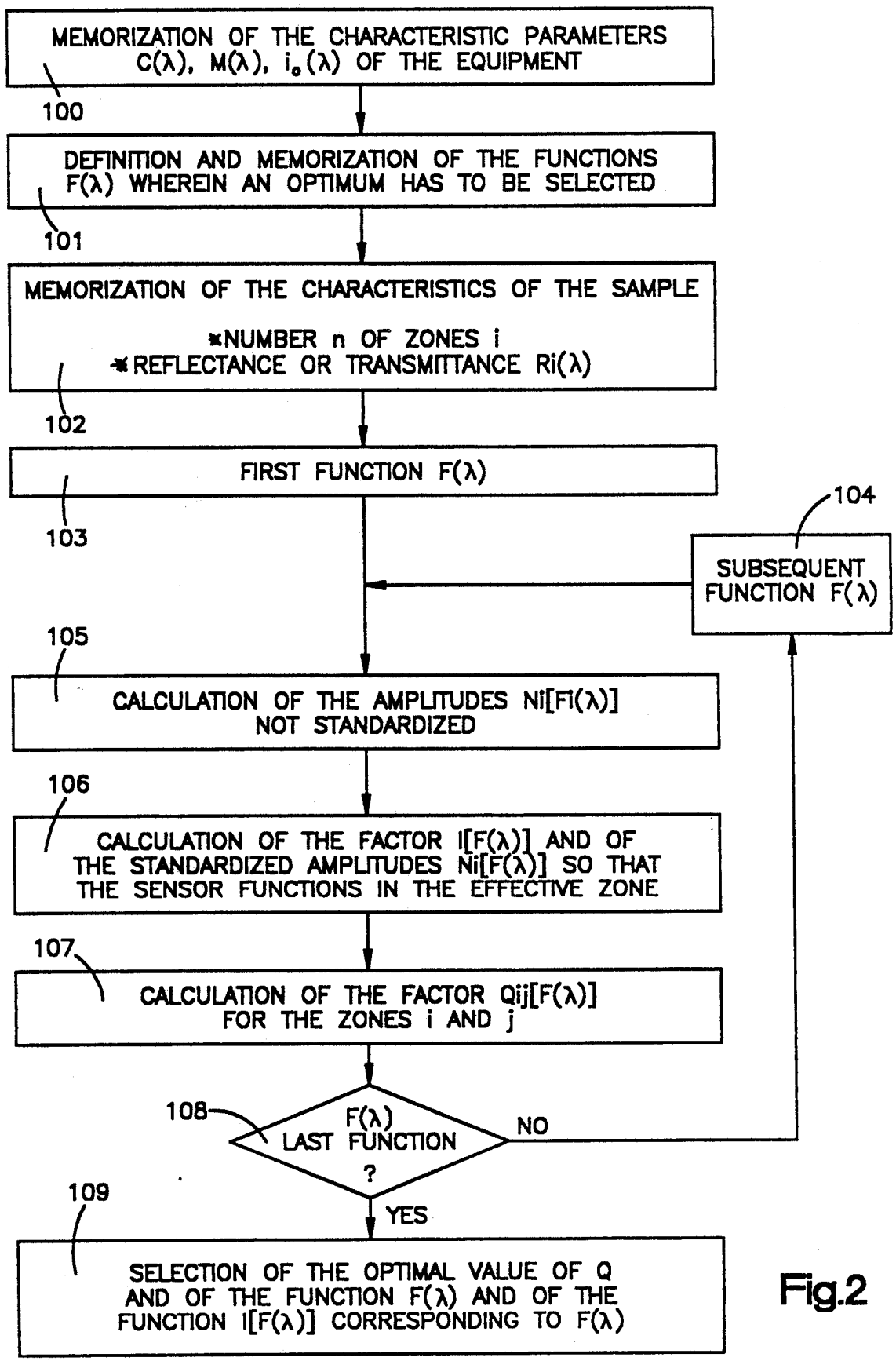
FIG. 2 is a flow chart of the main stages of the method of the invention.

According to this method, whose main stages are shown in FIG. 2, transmittance $F(\lambda)$ of a filter to be inserted between the microscope and the sample shall be selected so as to allow for optimization of contrast of the image of this sample.

In order to realize this, firstly two limiting wavelengths $\lambda A$ and $\lambda B$ are selected (selected according to the wavelength spectrum of the source of either the equipment or the sample) and, for different wavelengths between theses limiting wavelengths, as shown in stage 100 of the method, the characteristic parameters of the equipment are memorized:

$C(\lambda)$: the spectral response of the sensor. In fact, this spectral response is given by the sensor manufacturer, but it can also be obtained by preliminary standardization measurements which give, according to the wavelength, the amplitude of the sensor output signals as regards a predetermined intensity lighting.

M(λ): the spectral response of the microscope. This spectral response may be given by the microscope manufacturer or be obtained by preliminary standardization by determining, according to the wavelength, the power ratio of the luminous radiations supplied by the microscope to the power of the luminous radiations supplied to the microscope by the source.

io(λ) : the spectral density of the light source 7: this spectral density is the variation of the luminous power emitted by the source according to the wavelength ; it is given by the source manufacturer or determined by preliminary standardization of the source.

As stage 101 indicates, a definition is then made of all the filter transmittance functions F(λ) amongst which a search is made for the one which must procure optimal contrast between the n zones i of the sample to be controlled. As shall be seen subsequently in detail, obtaining of the transmittance function procuring optimal contrast makes it possible to select the desired transmittance filter between the source and the microscope. The transmittance function F(λ) is in fact the filter spectral response, i.e. the evolution according to the wavelength of the intensity of the light transmitted by the filter with respect to the intensity of the incident light. The definition of all the functions F(λ) depends on the available type of filtering means:

when the filtering means consists of a finite number of filters (for example a turret of filters), the function F(λ) is in this case firstly measured for each filter (by measuring for example for each filter the ratio of the intensity of the light transmitted by the filter to the intensity of the light received by o the latter). This function can also be supplied by the filter manufacturer, the filtering means may also be a filtering element whose function F(λ) may be adjusted within a wavelength interval (λA, λB) according to the various parameters; for example, in the case of a gaussian function, these parameters are the center wavelength (λo), the width Δλ and possibly the amplitude.

This filtering element is for example a variable passband interference filter whose center wavelength λo has been varied by moving the filter laterally in front of the source beam and whose width Δλ is varied by adjusting the beam diameter.

As stage 102 of the method shows, the main characteristics of the sample are then memorized, i.e. the number n of the zones i it comprises and its reflectance or transmittance coefficients Ri (λ) according to the wavelength. As indicated above, these coefficients are calculated from the respective optical parameters of the sample zones or measured by means of the spectrophotometer 13.

The signals supplied by this spectrophotometer for each of the sample zones and various wavelengths and which represent the reflectance or transmittance of the sample for each zone are recorded in the memory 12 of the microprocessor 11. The same applies to the other aforesaid parameters.

Reflectance or transmittance are measured without any filtering on the path of the luminous rays.

The sensor receives the image of a limited zone of the sample (microscope field).

The spectrophotometer receives the light reflected by an even more limited zone of the sample. In fact, reference zones, whose size is larger than the corresponding field of the spectrophotometer, need to be able to be found close to the inspected field. Measurement by spectrophotometry is effected prior to the taking of images of the sample field to be controlled.

For each function F(λ) (stages 103 and 104), a calculation is then made, from a first one of these functions (stage 103) for each of the n zones i to the sample to be controlled, of the amplitude values Ni (Fλ)) (stage 105), which would be equal to those of the output signals of the sensor with a transmittance filter F(λ). In this stage, it is not sought to yet calculate the "standardized" output signal amplitudes of the sensor corresponding to a function of the latter within an effective zone, namely to a nonsaturation of the sensor.

The values of the non-standardized amplitudes Ni*(F(λ)) are given in the following equation:

$$Ni^*(F(\lambda))) = I(F(\lambda)) \int_{\lambda A}^{\lambda B} C(\lambda) \cdot M(\lambda) \cdot F(\lambda) \cdot Ri(\lambda)i_o(\lambda)d\lambda \qquad (1)$$

The calculation program of this integral shall not be described in full since the calculation of this integral is known by experts, the microprocessor only considerably accelerating the calculation results.

In this equation, C(λ), M(λ), i (λ) are recorded in the memory during stage 100. F(λ) and Ri(λ) have been respectively memorized during stages 101 and 102.

For each function F(λ), a calculation is made (stage 106 called the standardization stage) of a corresponding attenuation factor I(F(λ)) of the source. This attenuation factor is the value of the luminous power supplied by the source divided by the maximum luminous power of this source (without attenuation). The values of standardized amplitudes Ni(F(λ) are given by the equation Ni(F(λ))=I(F(λ)) Ni*(Fλ)).

In order to calculate the attenuation factor, it is necessary to determine the adjustment of the source intensity so as to enable the sensor to function in the effective zone (sensor not saturated). The light intensity reaching the sensor must be neither too strong (since this would provoke saturation) nor too weak (since the output signal-to-noise ratio of the sensor would be too low). This operation can be regarded as "standardization" of the values of the amplitudes of the output signals of the sensor.

This standardization operation can be carried out by two different methods;

(A) - I(Fλ) may be calculated so that the maximum value Max Ni (for i varying from 1 to n) of the amplitudes Ni(F(λ)) of the sensor output signals is equal to a constant value $KN_{sat}$ with $0 \leq k \leq 1$, k being firstly fixed and $KN_{sat}$ being the value of the amplitude of the output signals corresponding to saturation of the sensor.

Therefore Max Ni = $Kn_{sat}$ i=1,n

In practice, K is chosen as being close to 0.8.

(B) - I(F(λ)) may also be calculated so that the average value of the amplitudes Ni(Fλ)) is equal to a predetermined constant value $kN_{sat}$.

Therefore:

$$\frac{1}{n} \sum_{i=1}^{n} Ni = kN_{sat}$$

In practice, K = ½ is selected

In order to calculate $I(F(\lambda))$, this is effected by starting with the non-standardized amplitude values $Ni^*(F(\lambda))$ given by the equation (1) and obtained in stage 105, and the following operation is carried out according to the selected method A or B:

Where method A is selected, the equation is thus resolved:

$$I(F(F(\lambda))) \max_{i=1,n} Ni^*(F(\lambda)) = kN_{sat}$$

Therefore:

$$I(F(\lambda)) = \frac{kN\,sat}{\max\limits_{i=1,n} Ni^*(F(\lambda))}$$

Where method B is selected, the equation is thus resolved:

$$\frac{I(F(\lambda))}{n} \sum_{i=1}^{n} Ni^*(F(\lambda)) = kN_{sat}$$

in which $$I(F(\lambda)) = \frac{k \cdot n \cdot N_{sat}}{\sum\limits_{i=1}^{n} Ni^*(F(\lambda))}$$

In (stage 107) for each function $F(\lambda)$ and for the sample zones i and j, calculation is made of the corresponding values $Q_{ij}$ of a contrast factor between these zones defined by the equation:

$$Q_{ij} = \frac{Ni - Nj}{N_{sat}}$$

with $1 \leq i \leq n$, $1 \leq j \leq n$ and $i < j$. The value $Q_{ij}$ is representative of the contrast between these two zones.

Stage 108 is a test consisting of determining if for the functions $F(\lambda)$ memorized in stage 101 the calculations effected in stages 105 to 107 for one of these functions are to be restarted for one next memorized function $F(\lambda)$ (answer NO to the question posed in stage 108), or if on the other hand, the function $F(\lambda)$ were the last memorized function (answer YES to the question posed in stage 108).

If the calculation of $Q_{ij}$ has just been effected for the last memorized function $F(\lambda)$, it will be necessary to search for the optimal quality factor Q which makes it possible to optimize contrast (stage 101). This search for the optimal value of the quality factor may be effected in different ways:

in the case where maximum contrast is desired to be obtained for each function $F(\lambda)$, the minimum value $Q_{ij}$ is selected from amongst the various couplings (i, j), and the function $F(\lambda)$ corresponding to the maximum value of these selected minimum values is then selected.

in the case where minimum contrast is desired to be obtained, for each function $F(\lambda)$ the maximum value $Q_{ij}$ is selected from amongst the various couplings (i, j) and the function $F(\lambda)$, which corresponds to the minimum value of the maximum selected values, is then selected.

In the case where contrast between two predetermined zones i and j are desired to be adjusted (such as for example the case of a sample having two zones $1=1$, $j=2$), the selection stage of one value $Q_{ij}$ for one given function $F(\lambda)$ is not necessary since each function $F(\lambda)$ corresponds to a single factor $Q_{ij}$. Thus, it merely needs to select $F(\lambda)$ corresponding to the desired value of $Q_{ij}$.

$I(F(\lambda))$ is also selected corresponding to the function $F(\lambda)$ which enables the optimal quality factor to be obtained.

Of course, the order of the various stages of the method may be modified. In particular, the selection of one quality factor from amongst the various factors $Q_{ij}$ for each function $F(\lambda)$ can be effected prior to stage 108, the selection of the optimal quality factor enabling the optimal function $F(\lambda)$ to be determined being then effected as previously described in stage 108.

Having thus determined the filter with the required pass-band, this filter can now be inserted onto the beam path between the source 7 and the microscope 4.

The required filter can be automatically selected by the microprocessor. The filtering device can for example be a mobile turret controlled by the microprocessor and comprising filters with various pass-bands. The microprocessor thus controls the movements of the turret so that the required filter is inserted onto the path of the luminous beam.

The filtering device can also be a variable passband interference filter controlled by the microprocessor which adjusts said pass-band.

In the case where a limited number of filters are disposed (such as in the case of the filter turret), the search for the optimal quality factor Q is effected from calculating various quality factors corresponding to the different filters of the turret.

In the case where the filtering device is a variable pass-band interference filter, the optimal quality factor Q is, for example, the one representing a maximum value from amongst the various quality Q factors calculated for all the possible filters.

What is claimed is:

1. A method for optimizing contrast in an image of a sample to be quality controlled having a whole number n of zones i, with $n > 2$, having various reflectance and transmittance coefficients, these zones being illuminated by a light source and the image obtained at the output of an optical system to be analyzed by a sensor supplying recording signals of this image on the outputs, comprising the following steps before obtaining the image of the sample:

defining a set of functions $F(\lambda)$ each representing transmittance according to the wavelength of an optical filter to be inserted between the source and the sample;

calculating for these functions $F(\lambda)$ the amplitudes values $Ni(F(\lambda))$ with $1 < i < n$ which would be equal to those of the corresponding output signals of the sensor respectively for each sample zone i with a transmittance filter $F(\lambda)$, these amplitudes $Ni(F(\lambda))$ being calculated from the equation:

$$Ni(F(\lambda)) = I(F(\lambda)) \int_{\lambda A}^{\lambda B} C(\lambda) \cdot M(\lambda) \cdot F(\lambda) \cdot Ri(\lambda)i_o(\lambda)d\lambda$$

in which the following parameters are known:
 $C(\lambda)$ denotes the sensor spectral response,
 $M(\lambda)$ denotes the spectral response of the optical system,
 $Ri(\lambda)$ denotes the reflectance or spectral transmittance of the zone i, $i_o(\lambda)$ denotes the power spectral density of the source, $\lambda A$ and $\lambda B$ are the two preliminarily selected limiting wavelengths, $I(F(\lambda))$ is the attenuation factor calculated for each of the functions $F(\lambda)$ so that the illumination power of the sample is compatible with the effective functioning zone of the sensor $(I(F(\lambda))$ and is between 0 and 1;

calculating for each function $F(\lambda)$ from the corresponding amplitudes Ni the values of one factor $Q_{ij}$ defined by the equation:

$$Q_{IJ} = \frac{Ni - Nj}{N_{sat}}$$

with $1 \leq i \leq n$ and $1 \leq j \leq n$ and $i < j$, each value of the factor $Q_{ij}$ being representative of the contrast between zones i and j and $N_{sat}$ denoting the signal amplitude with the highest value which the sensor can supply when it is saturated;

selecting for each function $F(\lambda)$ a value Q of the factor $Q_{ij}$ corresponding to the desired contrast and called the quality factor;

selecting from amongst the quality factors the quality factor Q allowing for the contrast to be optimized, this optimization supplying the transmittance $F(\lambda)$ of the filter to be selected; and inserting the selected filter between the source and the sample to be controlled so as to obtain the image of the sample.

2. Method as claimed in claim 1, wherein the parameters $C(\lambda)$, $M(\lambda)$, $i_o(\lambda)$ are respectively supplied by the sensor, the optical system and source or respectively calculated during preliminary standardization, $Ri(\lambda)$ being a parameter calculated from the optical parameters of each zone of the sample or measured by means of a spectrophotometer prior to controlling the sample.

3. Method as claimed in claim 2, wherein the attenuation factor or $I(F(\lambda))$ is calculated for each function $F(\lambda)$ so that the amplitude maximum value $Ni(F(\lambda))$ is equal to a constant value $K_{sat}$, with $0 < k \leq 1$, k being a predetermined value and $N_{sat}$ being the signal highest amplitude value which can be supplied by the saturated sensor.

4. Method as claimed in claim 2, wherein the power factor $I(F(\lambda))$ is calculated so that the amplitude average value $Ni(F(\lambda))$ is equal to a constant value $Kn_{sat}$, with $0 < k \leq 1$.

5. Method as claimed in either of claims 3 and 4, wherein the quality factor value Q allowing for optimization of the contrast is obtained by selecting for each function $F(\lambda)$ from amongst the values of factors $Q_{ij}$ the minimum value of $Q_{ij}$ and by choosing the function $F(\lambda)$ corresponding to the maximum of these minimum values of $Q_{ij}$.

6. Method as claimed in either of claims 3 and 4, wherein the quality factor value Q allowing for optimization of contrast is obtained by selecting for each function $F(\lambda)$ from amongst the values $Q_{ij}$ the maximum value of $Q_{ij}$ and by choosing the function $F(\lambda)$ corresponding to the minimum of the maximum values of $Q_{ij}$.

* * * * *

UNITED STATES PATENT AND TRADEMARK OFFICE
CERTIFICATE OF CORRECTION

PATENT NO.  : 4,991,970
DATED       : February 12, 1991
INVENTOR(S) : Darboux et al.

It is certified that error appears in the above-identified patent and that said Letters Patent is hereby corrected as shown below:

Column 3, line 48, delete "F $\lambda$)" and insert --F($\lambda$)--; and line 54, delete "F $\lambda$)" and insert --F($\lambda$)--.

Column 5, line 32, after "by" delete "o".

Column 6, line 6, delete "Ni(F$\lambda$)) and insert --Ni*(F $\lambda$))--.

15 - 19, between "$\lambda$B" and "$\lambda$A" insert --$\int$--.

Signed and Sealed this

First Day of September, 1992

Attest:

DOUGLAS B. COMER

*Attesting Officer*     *Acting Commissioner of Patents and Trademarks*